United States Patent [19]
Hahn

[11] Patent Number: 5,651,157
[45] Date of Patent: Jul. 29, 1997

[54] ELECTRIC TOOTHBRUSH WITH VIBRATION

[75] Inventor: Matthias Hahn, Frankfurt, Germany

[73] Assignee: Rowenta Werke GmbH, Offenbach A.M., Germany

[21] Appl. No.: 714,273

[22] Filed: Sep. 17, 1996

[30] Foreign Application Priority Data

Sep. 23, 1995 [DE] Germany .................. 29 51 5288.5

[51] Int. Cl.⁶ .................................................. A46B 13/02
[52] U.S. Cl. .................... 15/22.1; 15/167.1; 601/142; 601/70; 433/216; 433/122
[58] Field of Search .......................... 15/22.1, 22.2, 15/23, 24, 28, 29, 167.1; 433/216, 122, 123; 601/69, 141, 142, 67, 70, 68, 87; 132/322

[56] References Cited

U.S. PATENT DOCUMENTS

| | | |
|---|---|---|
| 3,466,689 | 9/1969 | Aurelio et al. .................. 601/142 |
| 3,685,080 | 8/1972 | Hubner ............................ 15/22.1 |
| 5,267,579 | 12/1993 | Bushberger ..................... 15/22.1 |
| 5,546,624 | 8/1996 | Bock ............................... 15/167.1 |

*Primary Examiner*—Gary K. Graham
*Attorney, Agent, or Firm*—Cohen, Pontani, Lieberman, Pavane

[57] ABSTRACT

An electric toothbrush having a handle with a cavity therein, a motor mounted in the cavity of the handle and having a rotatable shaft, a brush head, and a shaft arranged to connect the brush head to the handle. An eccentric weight is mounted to the motor shaft so as to rotate eccentrically when the motor shaft rotates so that the brush handle vibrates. A further weight is mounted to the shaft so as to be axially movable by a manipulator for adjusting vibration of the brush head.

2 Claims, 1 Drawing Sheet

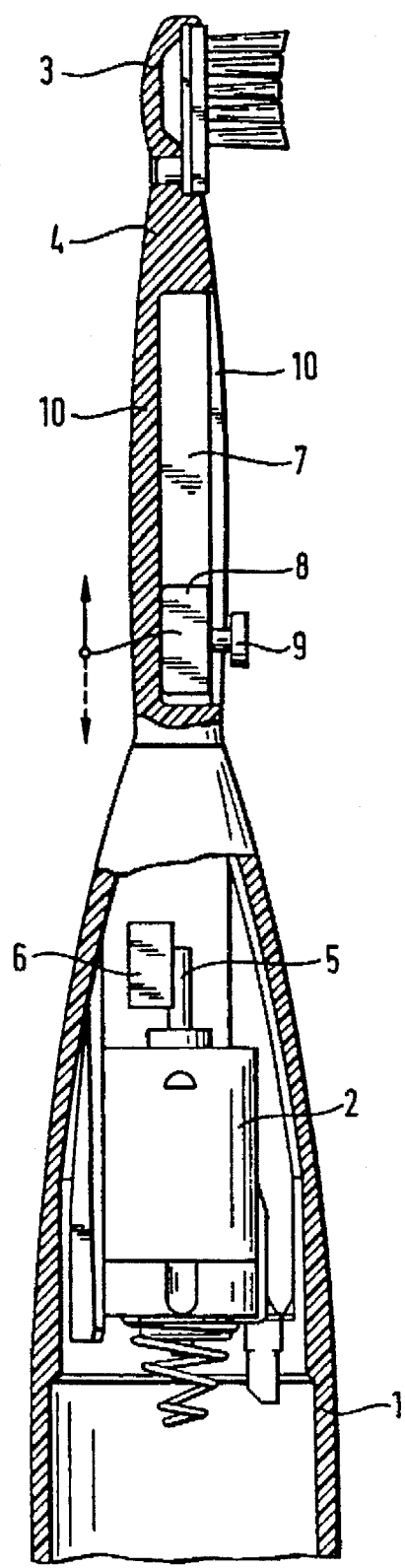

ELECTRIC TOOTHBRUSH WITH VIBRATION

BACKGROUND OF THE INVENTION

1. Field of the Invention

The invention relates to an electric toothbrush with a handle in which a motor is mounted, and a brush head. An eccentric weight is attached to the motor shaft and the eccentric rotation of the weight causes the brush head to vibrate.

2. Description of the Prior Art

A generic tooth cleaning device is known from U.S. Pat. No. 5,267,579. In this device, an eccentric weight is attached to the motor shaft and the vibrational intensity of the brush can be individually modified by regulating the speed of the motor. Regulating the motor speed means intervening in the electrical circuit and requires additional electrical components.

SUMMARY OF THE INVENTION

It is an object of the present invention to provide an electric toothbrush in which it is possible to individually mechanically modify the intensity of the brush head vibrations without great expense.

Pursuant to this object, and others which will become apparent hereafter, one aspect of the present invention resides in an electric toothbrush comprised of a handle having a cavity therein, a motor mounted in the cavity of the handle and having a rotatable shaft, a brush head, and a shaft arranged to connect the brush head to the handle. An eccentric weight is mounted on the motor shaft so as to rotate eccentrically when the motor shaft rotates so that the brush head vibrates. A further weight is mounted to the shaft so as to be axially movable by manipulator means. Axial movement of the further weight in the shaft results in changes in the vibration intensity of the brush head.

In another embodiment of the invention the shaft has a wall that defines an axially extending interior space. The further weight is arranged in the interior space and the manipulator means is connected to the further weight so as to extend through a slot in the shaft wall so as to permit the further weight to be moved by manipulation of the manipulator means.

The various features of novelty which characterize the invention are pointed out with particularity in the claims annexed to and forming a part of the disclosure. For a better understanding of the invention, its operating advantages, and specific objects attained by its use, reference should be had to the drawing and descriptive matter in which there are illustrated and described preferred embodiments of the invention.

BRIEF DESCRIPTION OF THE DRAWINGS

The single FIGURE shows a cross-section of an electric toothbrush pursuant to the present invention.

DETAILED DESCRIPTION OF THE PREFERRED EMBODIMENTS

As the drawing shows, the electric toothbrush of the present invention consists of a handle 1, in which a motor 2 is located, and a brush head 3, which is connected to the handle 1 by a shaft 4. Attached to the motor shaft 5 there is an eccentric weight 6, the eccentric rotation of which places the brush head 3 into vibration via the shaft 4 due to the unbalancing effect of the eccentric weight 6. The vibrational amplitude of the brush head 3 is determined by the geometry of the shaft 4, among other factors. A weight 8 is arranged movably in an empty space 7 in the shaft 4. A manipulator 9, which reaches through the wall 10 of the shaft 4, is arranged on the weight 8. The weight 8 can be axially moved within the empty space 7 by means of the manipulator 9, making it possible to modify the intensity of the brush head vibrations based on position of the weight 8.

The invention is not limited by the embodiments described above which are presented as examples only but can be modified in various ways within the scope of protection defined by the appended patent claims.

I claim:

1. An electric toothbrush, comprising: a handle having a cavity therein; a motor mounted in the cavity of the handle and having a rotatable motor shaft; a brush head; an elongated connecting shaft having a first end to which the brush head is connected, and a second end connected to the handle; a weight eccentrically mounted on the motor shaft with respect to the motor shaft axis so as to rotate eccentrically when the motor shaft rotates so that the brush head vibrates; a second weight mounted to the connecting shaft so as to be axially movable; and manipulator means for moving the second weight.

2. An electric toothbrush as defined in claim 1, wherein the connecting shaft has a wall that defines an axially extending interior space, the connecting shaft wall having a slot therein, the second weight being mounted to the connecting shaft in the interior space and the manipulator means being connected to the second weight so as to extend through the slot.

* * * * *